(12) United States Patent
Anderson

(10) Patent No.: US 10,099,862 B2
(45) Date of Patent: Oct. 16, 2018

(54) CONTAINER CONVEYOR APPARATUS WITH AN ADJUSTABLE RAILING

(71) Applicant: Owens-Brockway Glass Container Inc., Perrysburg, OH (US)

(72) Inventor: William P. Anderson, Toledo, OH (US)

(73) Assignee: Owens-Brockway Glass Container Inc., Perrysburg, OH (US)

( * ) Notice: Subject to any disclaimer, the term of this patent is extended or adjusted under 35 U.S.C. 154(b) by 0 days.

(21) Appl. No.: 15/459,777

(22) Filed: Mar. 15, 2017

(65) Prior Publication Data

US 2018/0265301 A1   Sep. 20, 2018

(51) Int. Cl.
| | |
|---|---|
| *B65G 21/20* | (2006.01) |
| *B65G 29/00* | (2006.01) |
| *B65G 47/84* | (2006.01) |
| *G01N 33/38* | (2006.01) |
| *G01N 3/00* | (2006.01) |
| *G01N 33/00* | (2006.01) |

(52) U.S. Cl.
CPC ......... *B65G 21/2072* (2013.01); *B65G 29/00* (2013.01); *B65G 47/846* (2013.01); *G01N 3/00* (2013.01); *G01N 33/386* (2013.01); *B65G 2201/0235* (2013.01); *G01N 2033/0081* (2013.01)

(58) Field of Classification Search
CPC ............... B65G 21/2072; B65G 29/00; B65G 2201/0244; B65G 2207/08; B65G 47/846; G01N 3/00; G01N 3/08; G01N 2033/0081; G01N 33/386
See application file for complete search history.

(56) References Cited

U.S. PATENT DOCUMENTS

| | | | | |
|---|---|---|---|---|
| 3,168,370 A | | 11/1971 | Dubble et al. | |
| 3,628,379 A | | 12/1971 | Babunovic | |
| 3,702,563 A | * | 11/1972 | Brady | G01N 3/00 73/12.01 |
| 3,729,082 A | * | 4/1973 | Federko | B23Q 11/08 141/97 |
| 3,765,231 A | * | 10/1973 | Erb | G01N 3/00 73/824 |

(Continued)

FOREIGN PATENT DOCUMENTS

| | | |
|---|---|---|
| EP | 1758804 | 3/2007 |
| FR | 1459406 A | 4/1966 |

OTHER PUBLICATIONS

PCT Search Report and Written Opinion, Int. Serial No. PCT/US2018/018874, Int. Filing Date: Feb. 21, 2018 Applicant: Owens-Brockway Glass Container Inc., dated May 16, 2018.

*Primary Examiner* — Gene O Crawford
*Assistant Examiner* — Keith R Campbell

(57) ABSTRACT

A container conveyor apparatus that conveys containers along a container path includes a front rail of an adjustable railing apparatus that is arcuately shaped along a container path and forms part of a surface facing radially inwardly; and a rear rail of the adjustable railing apparatus that is arcuately shaped along the container path and forms another part of the surface facing radially inwardly; the front rail and the rear rail of the adjustable railing apparatus move with respect to one another to change the width of the container path and accommodate containers of different sizes.

18 Claims, 4 Drawing Sheets

(56) References Cited

U.S. PATENT DOCUMENTS

| | | | |
|---|---|---|---|
| 3,777,556 A * | 12/1973 | Zappia | G01N 3/00 73/825 |
| 3,885,421 A * | 5/1975 | Nakamura | G01N 3/00 73/824 |
| 4,021,122 A | 5/1977 | Krenmayr | |
| 4,075,086 A | 2/1978 | Marsh, III et al. | |
| 4,077,254 A | 3/1978 | Mercer, Jr. et al. | |
| 4,096,939 A | 6/1978 | Riggs et al. | |
| 4,201,621 A | 5/1980 | Crankshaw et al. | |
| 4,479,582 A | 10/1984 | Ducloux | |
| 4,624,098 A | 11/1986 | Trendel | |
| 5,082,105 A * | 1/1992 | Tincati | B65G 47/846 198/473.1 |
| 5,351,552 A * | 10/1994 | Giometti | G01M 99/007 209/599 |
| 5,540,320 A * | 7/1996 | Sarto | B67C 7/0046 198/473.1 |
| 6,172,355 B1 | 1/2001 | Gast et al. | |
| 7,748,523 B2 * | 7/2010 | Robertson | B65G 21/2072 198/831 |
| 7,967,127 B2 * | 6/2011 | Spence | B65G 29/00 198/459.2 |
| 8,205,740 B2 | 6/2012 | Dragon et al. | |
| 8,499,921 B1 * | 8/2013 | Orndorff | B65G 21/2072 198/479.1 |
| 8,813,950 B2 * | 8/2014 | Papsdorf | B65G 29/00 198/473.1 |
| 8,820,514 B2 * | 9/2014 | Papsdorf | B65G 29/00 198/478.1 |
| 9,340,364 B2 * | 5/2016 | Papsdorf | B65G 29/00 |
| 2008/0116042 A1 | 5/2008 | McAlister | |
| 2009/0175691 A1 | 7/2009 | Hirschek | |
| 2011/0127143 A1 * | 6/2011 | Calzolari | B65G 21/2072 198/618 |
| 2016/0194155 A1 * | 7/2016 | Doherty | B65G 29/00 198/723 |

* cited by examiner

CONTAINER CONVEYOR APPARATUS WITH AN ADJUSTABLE RAILING

The present disclosure relates to container conveyor apparatuses and, more particularly, to adjustable railings used with the container conveyor apparatuses.

BACKGROUND

Inspection apparatuses inspect containers as they travel from one area of a container processing facility to another. Inspection includes pressure testing containers as they pass through a pressure test inspection system. Inspection apparatuses include an infeed roller and a container path that transport containers into contact with both a pressure roller and moveable pressure pad. As the container contacts the pressure roller and moveable pressure pad, the pad exerts a force against the container toward the pressure roller. The pressure roller resists this force thereby transferring it to the container and testing its resiliency. Containers that successfully withstand the force without breaking are then conveyed away from the pressure roller/moveable pressure pad and toward a outfeed roller.

The container conveyors that can be used by inspection apparatuses function well when the diameter of the received containers falls within a limited range. Containers having a common design, diameter, or both can be easily received by the container conveyors. However, when containers have significantly different diameters, the container conveyors may need to be stopped and reconfigured to accommodate differently sized containers. A loss of productivity exists during the reconfiguration of container conveyors. It would be helpful to provide a container conveyor that adjusts to containers of different diameters without machine stoppages, time-consuming reconfiguration, or both.

SUMMARY OF THE DISCLOSURE

In one embodiment, a container conveyor apparatus conveys containers along a container path. The apparatus includes a front rail of an adjustable railing apparatus that is arcuately shaped along a container path and forms part of a surface facing radially inwardly; and a rear rail of the adjustable railing apparatus that is arcuately shaped along the container path and forms another part of the surface facing radially inwardly; the front rail and the rear rail of the adjustable railing apparatus move with respect to one another to change the width of the container path and accommodate containers of different sizes.

In another embodiment, a glass container conveyor apparatus conveys containers along a container path. The apparatus includes an infeed roller; an outfeed roller downstream of the infeed roller; a pressure roller between the infeed roller and the outfeed roller; a pressure pad downstream of the infeed roller and upstream of the outfeed roller; an infeed front rail and infeed rear rail upstream of the pressure pad; and an outfeed front rail and outfeed rear rail downstream of the pressure pad.

In yet another embodiment, a container conveyor apparatus conveys containers along a container path. The apparatus includes a front rail having an arcuate rail slot; a rear rail that is pivotably coupled to the front rail via a rail pivot that extends through the arcuate rail slot permitting the front rail and the rear rail to move with respect to one another to change the width of the container path accommodating containers of different sizes; and a pressure pad pivot that pivotably couples the rear rail to a pressure pad of the container conveyor apparatus.

BRIEF DESCRIPTION OF THE DRAWINGS

The disclosure may best be understood from the following description, the appended claims, and the accompanying drawings, in which:

DETAILED DESCRIPTION

Container conveyor apparatuses can use an adjustable railing apparatus to receive differently-sized containers having a wide range of diameters without machine stoppage or lengthy reconfiguration of the container conveyor apparatus. The container conveyor apparatus can include a plurality of rollers that rotate to draw a container along a container path. As the apparatus receives a container, the adjustable railing apparatus opposite the rollers can move closer to or further away from those rollers to accommodate containers having different diameters without having to stop the container conveyor apparatus or manually adjust the container conveyor apparatus. In some implementations, the container conveyor apparatuses can flexibly receive containers having diameters ranging from $1\frac{1}{2}$-$2\frac{7}{8}$ inches, $2\frac{13}{16}$-$4\frac{3}{16}$ inches, $4\frac{1}{16}$-$5\frac{7}{16}$ inches, or $5\frac{3}{8}$-$6\frac{3}{4}$ inches.

Figure 1:
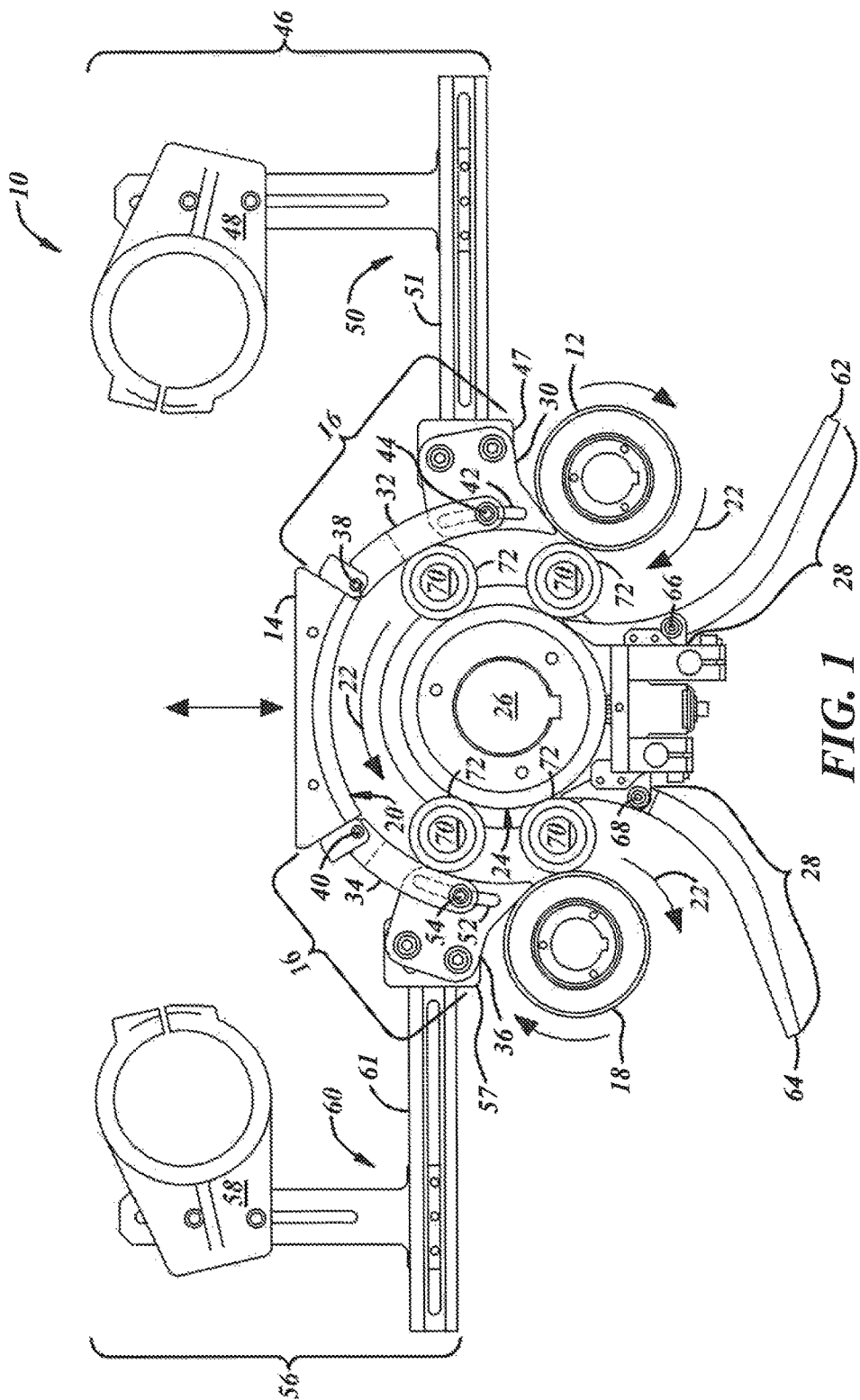
FIG. 1 is a plan view of one embodiment of a container conveyor apparatus.

FIG. 1 illustrates a plan view of one embodiment of a container conveyor apparatus 10. The container conveyor apparatus 10 can include an infeed roller 12, a pressure pad 14, an inner portion 16 of a multipart adjustable railing apparatus pivotably linked to the pressure pad 14, and an outfeed roller 18 each located along a first side 20 of a container path 22. The first side 20 of the container path 22 is a first surface that contacts the container as it travels. The other side 24 of the container path 22 includes include a pressure roller 26 and an outer portion 28 of the multipart adjustable railing apparatus that can be positioned adjacent to the pressure roller 26 and opposite to the infeed roller 12 and outfeed roller 18 as well as side 20. The other side 24 of the container path 22 is a second surface that contacts the container as it travels.

The inner portion 16 and outer portion 28 of the multipart adjustable railing apparatus can each comprise assemblies of more than one element movably linked with each other. The inner portion 16 can include an infeed front rail 30, an infeed rear rail 32, an outfeed rear rail 34, and an outfeed front rail 36. These elements have been identified by the order in which a container will pass by them; they can provide the side 20 that faces and contacts containers as they pass through the apparatus 10. The infeed front rail 30 and the infeed rear rail 32 can form a subassembly that is pivotably attached to the pressure pad 14 via a first pressure pad pivot 38 while the outfeed rear rail 34 and the outfeed front rail 36 can form a separate subassembly that is pivotably attached to the pressure pad 14 via a second pressure pad pivot 40.

The infeed front rail 30 can include an infeed rail slot 42 that receives an infeed rail pivot 44. The infeed rail slot 42 can be implemented as an arcuate void in the rail 30 that is sized to receive the pivot 44 that passes through the slot 42. However, it should be appreciated that shapes other than the arcuate one shown can also be used. The infeed rail pivot 44 can be fixedly held by the infeed rear rail 32 and pass through the slot 42 so that the slot 42 and the pivot 44 allow the infeed rear rail 32 to move with respect to the infeed front rail 30. More specifically, the pivot 44 can be implemented as a fastener in the form of a pin or a bolt having a nut screwed on one end that permits the infeed front rail 30 to both slide along the infeed rail slot 42 as well as pivot about the pin or bolt/nut relative to the infeed rear rail 32.

The infeed front rail 30 is also attached to an infeed adjustment linkage 46 at a location on the rail 30 that is opposite the infeed rail slot 42. The infeed front rail 30 can be connected to an arm 51 of the adjustment linkage 46 via an adjustment plate 47 and an infeed nut plate using bolts. The adjustment linkage 46 can include an adjustment plate 47 at one end that is sandwiched between the infeed front rail 30 and the infeed nut plate. The infeed front rail 30 can include two holes while the adjustment plate 47 may include two arcuate slots. Bolts pass through the holes of the infeed front rail 30 and the arcuate slots of the adjustment plate 47 and are ultimately received by the infeed nut plate. This arrangement is discussed in greater detail below and shown with reference to FIG. 5. The infeed adjustment linkage 46 can include a rotational adjustment member 48 and an infeed linkage 50 that translates movement by the infeed front rail 30 into rotational movement by the rotational adjustment member 48. It is possible to implement the infeed adjustment linkage 46 as a single member or as an assembly of a plurality of members that are rigidly or flexibly attached to each other.

The separate subassembly that includes the outfeed rear rail 34 and the outfeed front rail 36 can include an outfeed rail slot 52 receiving an outfeed rail pivot 54 that is similar to the infeed rail slot 42 and infeed pivot 44. The outfeed rail pivot 54 can be fixedly held by the outfeed rear rail 34 and pass through the outfeed rail slot 52 so that the slot 52 and the pivot 54 allow the outfeed front rail 36 to move with respect to the outfeed rear rail 34. As with the infeed rail pivot 44, the outfeed rail pivot 54 can be implemented as a fastener in the form of a pin or a bolt having a nut screwed on one end that permits the outfeed front rail 36 to both slide along the outfeed rail slot 52 as well as pivot about the pin or bolt/nut relative to the outfeed rear rail 34.

The outfeed front rail 36 can also be attached to an outfeed adjustment linkage 56 at a location on the rail 36 that is opposite the outfeed rail slot 52. The outfeed front rail 36 can be connected to an arm 61 of the outfeed adjustment linkage 56 via an outfeed adjustment plate 57 and an outfeed nut plate using bolts. The adjustment linkage 56 can include an adjustment plate 57 at one end that is sandwiched between the outfeed front rail 36 and the outfeed nut plate. The outfeed front rail 36 can include two holes while the adjustment plate 57 may include two arcuate slots. Bolts pass through the holes of the outfeed front rail 36 and the arcuate slots of the adjustment plate 57 and are ultimately received by the outfeed nut plate.

The outer portion 28 of the multipart adjustable railing apparatus can include an outer infeed rail 62 and an outer outfeed rail 64. Both the outer infeed rail 62 and the outer outfeed rail 64 can be arcuately shaped and pivotably attached to the apparatus 10. These elements can provide the second side 24 of the container path 22; the second side is a second surface that faces and contacts the containers as they pass along the container path 22 through the apparatus 10. The outer infeed rail 62 moves closer to or further from the infeed roller 12 about an outer infeed pivot 66 and the outer outfeed rail 64 moves closer to or further from the outfeed roller 18 about an outer outfeed pivot 68 depending on the diameter of containers received by the apparatus 10

As the container conveyor apparatus 10 receives a container 70 having a particular diameter, the container 70 can intially be handled by the outer portion 28 of the multipart adjustable railing apparatus. The outer infeed rail 62 can move about the outer infeed pivot 66 to accommodate containers having different diameters so that both the outer infeed rail 62 and the infeed roller 12 contact an outer surface 72 of the container 70. The outer infeed rail 62 can move about the outer infeed pivot 66 away from the infeed roller 12 to accommodate larger diameter containers and the outer infeed rail 62 can move toward the infeed roller 12 when the apparatus 10 receives smaller diameter containers. When the outer surface 72 of the container 70 contacts the rotating infeed roller 12, the container 70 rotates and begins to roll along a surface of the outer infeed rail 62 as the container 70 travels through the container conveyor apparatus 10 along the container path 22. The outer infeed rail 62 can pivot about the outer infeed pivot 66 so that both the surface of the infeed rail 62 and the infeed roller 12 touch the outer surface 72 of the container 70 at the same time.

After being moved along the container path 22 while guided by the outer infeed rail 62 and the infeed roller 12, the container 70 begins to be moved by the pressure roller 26 and the inner portion 16 of the adjustable railing apparatus. An outer surface of the rotating pressure roller 26 can press against the outer surface 72 of the container 70. The infeed front rail 30 and the infeed rear rail 32 can pivot about the first pressure pad pivot 38, the infeed rail pivot 44, or both to size the container path 22 such that the rails 30, 32 touch the outer surface 72 of the container 70 at the same time the pressure roller 26 presses against the outer surface 72. The rotation of the pressure roller 26 rolls the container 70 along the infeed front rail 30 and the infeed rear rail 32.

As the container 70 moves along the container path 22, the container 70 becomes positioned between the pressure roller 26 and the pressure pad 14. After the container 70 contacts both the pressure roller 26 and the pressure pad 14, the apparatus 10 exerts a force on the container 70 through the pressure pad 14 and toward the pressure roller 26 thereby squeezing the container 70. The pressure pad 14 can be moved toward the container 70 and the pressure roller 26 with an amount of force designed to test the quality of the containers. In particular, the amount of force exerted by the pressure pad 14 can be designed to test the resiliency of containers made of glass. However, it should be appreciated that the amount of force exerted by the apparatus 10 on a container using the pressure pad 14 can be set to test containers made from other material types. Containers that suffer from one or more structural defects may not withstand the applied force intact and fail. Otherwise, containers that adequately resist the force applied by the pressure pad 14 can move to an area along the container path 22 where the pressure roller 26 opposes the outfeed rear rail 34 and an outfeed front rail 36.

The outfeed rear rail 34 and outfeed front rail 36 can be configured like the infeed front rail 30 and infeed rear rail 32 discussed above. The outfeed rear rail 34 and the outfeed front rail 36 can be pivotably attached to each other as well as to the pressure pad 14 and collectively move closer to or away from the pressure roller 26 in response to the diameter of the container passing through the container path 22. The container 70 moves along the outfeed rear rail 34 and the outfeed front rail 36 until it contacts the outfeed roller 18. The outside surface 72 of the container 70 contacts both the outfeed roller 18 and the outer outfeed rail 64. The outer outfeed rail 64 pivots about the outer outfeed pivot 68 so that the rail 64 moves closer to the outfeed roller 18 when the diameter of the container is smaller and away from the outfeed roller 18 when the diameter of the container is larger as is described above with respect to the outer infeed rail 62. The rotational movement of the outfeed roller 18 can continue to move the container 70 along the container path 22 as it rolls against the outer outfeed rail 64. The outfeed roller 18 moves the container 70 such that it is held between the roller 18 and the outer outfeed rail 64. The outer outfeed rail 64 functions like the outer infeed rail described above such that it can pivot relative to the outfeed roller 18 and accommodate varying diameter containers. Some elements of the container conveyor apparatus 10 will be discussed in greater detail below.

Figure 2:
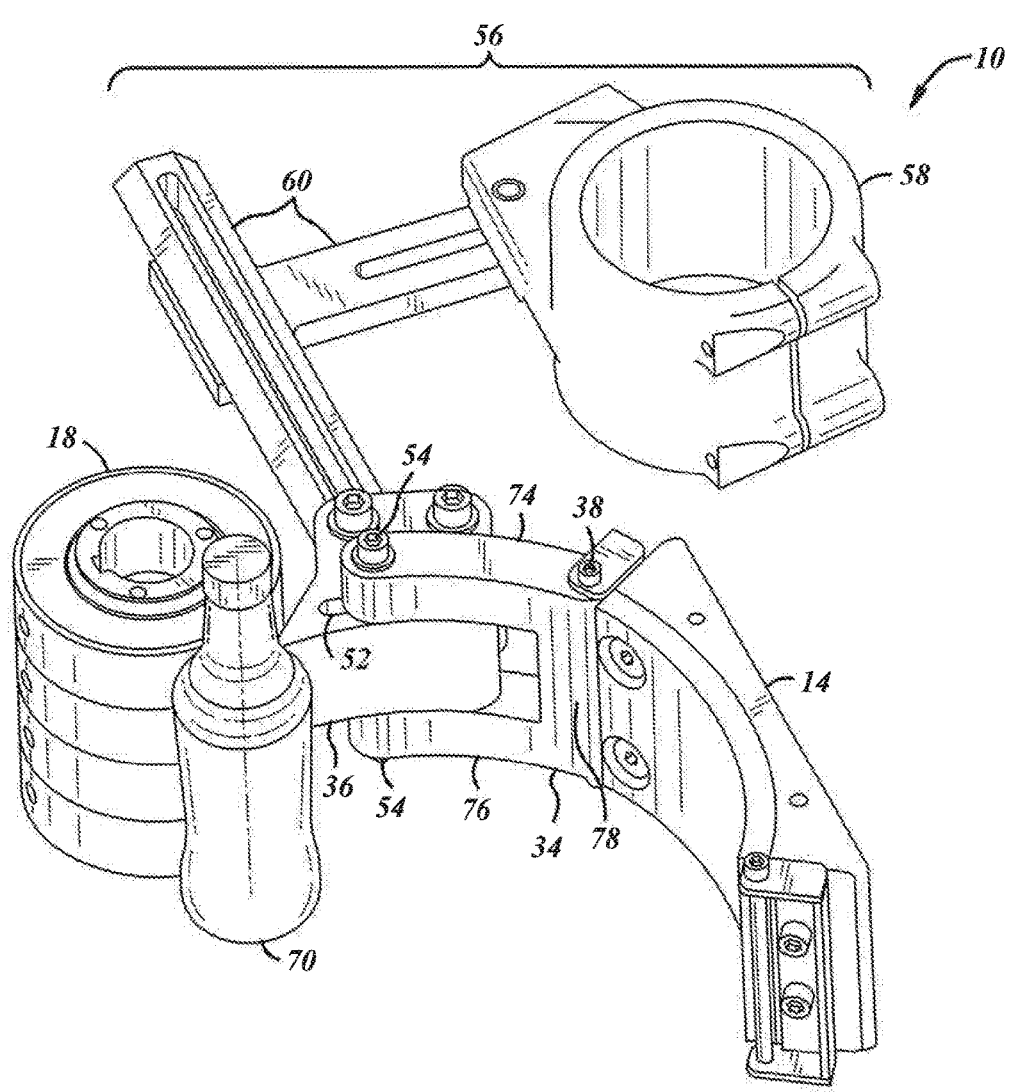
FIG. 2 is a perspective view of a portion of the container conveyor apparatus shown in FIG. 1.

Turning to FIG. 2, a portion of the container conveyor apparatus 10 is shown in a perspective view. This view depicts the pressure pad 14, the outfeed rear rail 34, and the outfeed front rail 36 along with the outfeed roller 18 and the outfeed adjustment linkage 56. The outfeed rear rail 34 includes an upper member 74 and a lower member 76 that oppose each other and are rigidly fixed together by a connecting portion 78 at one end. The upper member 74 and the lower member 76 can be oriented in a stacked relationship with the upper member 74 located above the lower member 76 such that they at least partially overlap. In some implementations, the upper member 74 and the lower member 76 are arcuately shaped. However, it should be appreciated that the upper member 74 and the lower member 76 can be differently shaped. At least a portion of the outfeed front rail 36 and its outfeed rail slot 52 can be received between the upper member 74 and the lower member 76. The outfeed rail pivot 54 may pass between the upper member 74 and the lower member 76 and through the outfeed rail slot 52.

Figure 3:
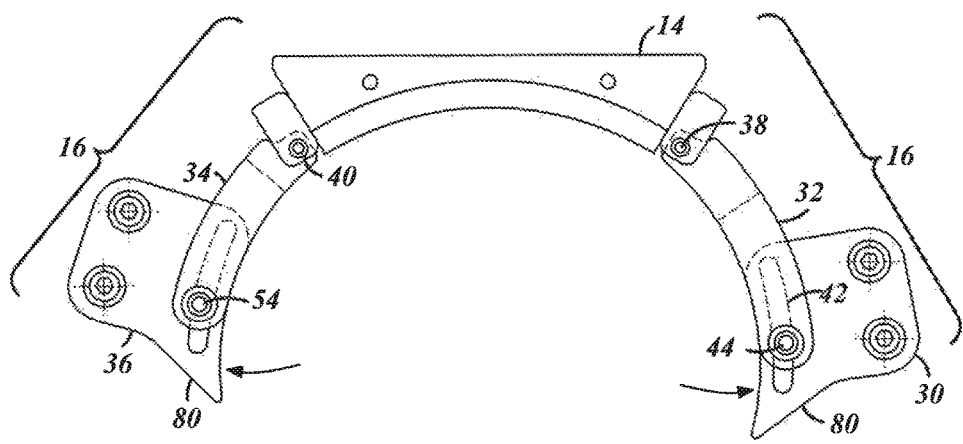
FIG. 3 is a plan view of a portion of the container conveyor apparatus shown in FIG. 1 as it exists in one position.
Figure 4:
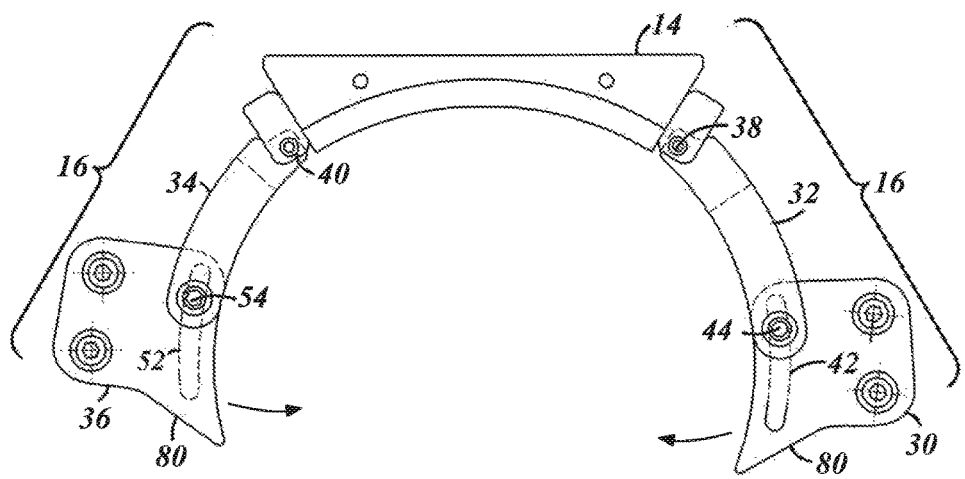
FIG. 4 is a plan view of a portion of the container conveyor apparatus shown in FIG. 1 as it exists in another position and FIG. 5 is an exploded view of a portion of the container conveyor apparatus shown in FIG. 1

FIGS. 3-4 depict an implementation of the inner portion 16 of the multipart adjustable railing apparatus in different positions. FIG. 3 depicts the inner portion 16 in a retracted position that can accommodate containers of relatively larger diameters. In contrast, FIG. 4 depicts the inner portion 16 in an expanded position that can accommodate containers of relatively smaller diameters. With respect to the adjustable railing apparatus shown in FIG. 3, the infeed front rail 30 and the outfeed front rail 36 are moved closer toward the first pressure pad pivot 38 and the second pressure pad pivot 40, respectively. In this position, the infeed rail pivot 44 and the outfeed rail pivot 54 are located closer to distal ends 80 of the front rails thereby increasing the width of the container path. FIG. 4 depicts the infeed front rail 30 and the outfeed front rail 36 moved away from the first pressure pad pivot 38 and the second pressure pad pivot 40, respectively. In this position, the infeed rail pivot 44 and the outfeed rail pivot 54 are located further away from distal ends 80 of the front rails thereby decreasing the width of the container path.

Figure 5:
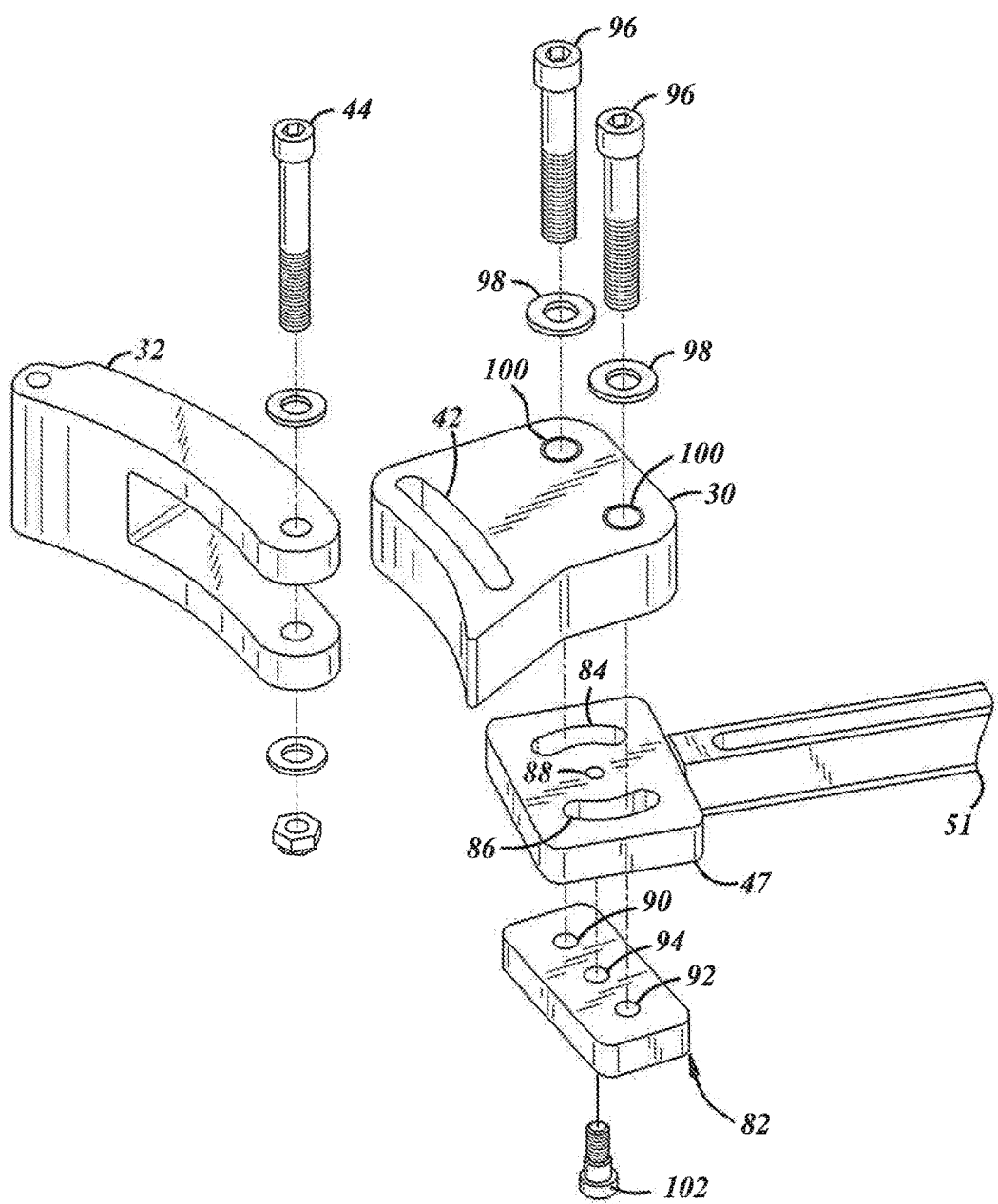

Turning to FIG. 5, an exploded view of the infeed front rail 30 and infeed rear rail 32 is shown along with the infeed adjustment plate 47 and an infeed nut plate 82. The infeed adjustment plate 47 is attached to an end 51 of the adjustment linkage 46 and the infeed adjustment plate 47 is located in between the infeed front rail 30 and the infeed nut plate 82. The infeed adjustment plate 47 may include a first arcuate slot 84, a second arcuate slot 86, and a threaded receptacle 88. The infeed nut plate 82 can be mounted to the infeed adjustment plate 47 and include a first threaded nut plate receptacle 90, a second threaded nut plate receptacle 92, and an unthreaded nut plate aperture 94. Bolts 96 can be used with washers 98 and pass through holes 100 in the infeed front rail 30 as well as the first and second arcuate slots 84, 86. Threaded ends of the bolts 96 can engage the first threaded nut plate receptacle 90 and the second threaded nut plate receptacle 92. The infeed nut plate 82 and infeed front rail 30 can pivot together relative to the infeed adjustment plate 47 about a bolt 102 passing through the unthreaded nut plate aperture 94 and received by the threaded receptacle 88 in a range of motion defined by the bolts 96 moving within the first arcuate slot 84 and the second arcuate slot 86. After the infeed nut plate 82 and infeed front rail 30 are moved to their desired position relative to the infeed adjustment plate 47, the infeed nut plate 82 can be rigidly fixed against the infeed adjustment plate 47 by tightening the bolts 96 that pass through the arcuate slots 84, 86 and the bolt 102. The infeed front rail 30 can include the infeed rail slot 42 that receives the infeed rail pivot 44 as is discussed above with respect to FIG. 1.

It is to be understood that the foregoing is a description of one or more embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "e.g.," "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A container conveyor apparatus that conveys containers along a container path, the apparatus comprising:
    a front rail of an adjustable railing apparatus that is arcuately shaped along a container path and forms part of a surface facing radially inwardly; and
    a rear rail of the adjustable railing apparatus that is arcuately shaped along the container path and forms another part of the surface facing radially inwardly,
    wherein the front rail and the rear rail are linked with each other via a pivot extending through portions of the front rail and the rear rail, and wherein the front rail and the rear rail of the adjustable railing apparatus move and pivot with respect to one another to change the width of the container path and accommodate containers of different sizes.

2. The apparatus of claim 1, wherein the front rail or the rear rail includes a slot.

3. The apparatus of claim 2, wherein the slot is arcuately shaped and the pivot includes a fastener.

4. The apparatus of claim 1, wherein the rear rail comprises a first rear rail member and a second rear rail member that are spaced apart and connected by a connecting portion located in between the first rear rail member and the second rear rail member.

5. The apparatus of claim 4, wherein a portion of the front rail is disposed between the first rear rail member and the second rear rail member.

6. The apparatus of claim 1, wherein the front rail and the rear rail are adjacent to a roller.

7. The apparatus of claim 1, wherein the front rail and the rear rail are pivotably coupled to a pressure pad.

8. The apparatus of claim 1, wherein the containers are made of glass.

9. A glass container conveyor apparatus that conveys containers along a container path, the apparatus comprising:
an infeed roller;
an outfeed roller downstream of the infeed roller;
a pressure roller between the infeed roller and the outfeed roller;
a pressure pad downstream of the infeed roller and upstream of the outfeed roller;
an infeed front rail and infeed rear rail upstream of the pressure pad; and
an outfeed front rail and outfeed rear rail downstream of the pressure pad;
wherein one of the infeed front rail and the infeed rear rail comprises a first infeed rail member and a second infeed rail member that are spaced apart and connected by a connecting portion located in between the first infeed rail member and the second infeed rear member, and a portion of the other of the infeed front rail and the infeed rear rail is disposed between the first infeed rail member and the second infeed rail member, and wherein one of the infeed front rail and the infeed rear rail includes a slot to receive a pivot extending through portions of the infeed front and rear rails, and wherein the infeed front and rear rails both slide and pivot with respect to one another.

10. The apparatus of claim 9, wherein the infeed rear rail is pivotably coupled to an upstream end of the pressure pad and the outfeed rear rail is pivotably coupled to a downstream end of the pressure pad.

11. The apparatus of claim 9, wherein the pressure pad squeezes containers toward the pressure roller and exerts a force on containers travelling along a container path in an amount that breaks containers having one or more structural defects.

12. The apparatus of claim 9, wherein the infeed front rail and the infeed rear rail are linked with each other via a pivot, and the other of the infeed front rail and the infeed rear rail includes an arcuately shaped slot wherein the pivot extends through the slot such that the one of the infeed front rail and the infeed rear rail is translatable along the slot and also pivotable about an axis of the pivot.

13. A container conveyor apparatus that conveys containers along a container path, the apparatus comprising:
a front rail having an arcuate rail slot;
a rear rail that is pivotably coupled to the front rail via a rail pivot that extends through the arcuate rail slot permitting the front rail and the rear rail to move and pivot with respect to one another to change the width of the container path accommodating containers of different sizes; and
a pressure pad pivot that pivotably couples the rear rail to a pressure pad of the container conveyor apparatus.

14. The apparatus of claim 13, further comprising: an outer rail that is pivotably attached to the apparatus and moves closer to and further from a roller based on a diameter size of a container.

15. The apparatus of claim 13, wherein the rear rail comprises a first rear rail member and a second rear rail member that are spaced apart and connected by a connecting portion located in between the first rear rail member and the second rear rail member.

16. The apparatus of claim 15, wherein a portion of the front rail is disposed between the first rear rail member and the second rear rail member.

17. The apparatus of claim 13, further comprising: an infeed roller, an outfeed roller, and a pressure roller.

18. The apparatus of claim 13, wherein the containers are made of glass.

* * * * *